United States Patent [19]
Reber

[11] Patent Number: 5,021,666
[45] Date of Patent: Jun. 4, 1991

[54] PASS-LINE INDEPENDENT WEB MEASURING METHOD AND APPARATUS

[75] Inventor: Eric J. Reber, Rockford, Ill.

[73] Assignee: Barber-Colman Company, Rockford, Ill.

[21] Appl. No.: 407,417

[22] Filed: Sep. 14, 1989

[51] Int. Cl.$^5$ .......................... G01T 7/00; G01B 7/04; G01N 23/16

[52] U.S. Cl. .............................. 250/359.1; 250/360.1; 250/308; 250/341

[58] Field of Search ................. 250/359.1, 360.1, 308, 250/341

[56] References Cited

U.S. PATENT DOCUMENTS

| | | | |
|---|---|---|---|
| 3,828,190 | 8/1974 | Dahlin et al. | 250/308 |
| 4,276,480 | 6/1981 | Watson | 250/560 |
| 4,845,730 | 7/1989 | Mercer | 378/53 |

FOREIGN PATENT DOCUMENTS

| | | | |
|---|---|---|---|
| 59-18413 | 1/1984 | Japan | 250/308 |
| 86047432 | 7/1985 | U.S.S.R. | 250/308 |

OTHER PUBLICATIONS

Sep. 1985, "Indev Web Measurement, Control and Process Management", Published by Barber-Colman Indev.

"Betamike ® O-Frame Measurement Subsystem", published by Barber-Colman Indev.

Primary Examiner—Constantine Hannaher
Assistant Examiner—Jacob M. Eisenberg
Attorney, Agent, or Firm—Leydig, Voit & Mayer

[57] ABSTRACT

A pass-line independent measuring device for producing thickness related measurements (e.g., thickness, basis weight, density, etc.) of a moving web. The thickness measurements themselves are based on a nuclear source and detector mounted on one or both sides of the web, the source emitting radiation and the detector detecting emitted radiation from the web as an uncorrected measure of web thickness. An ultrasonic distance measuring means is fixedly associated with either the source, the detector, or both and continuously directs ultrasonic pulses in a direct path to the web, measures reflections in substantially a similar direct path, and by means of the time delay between a pulse and its reflection determines the actual pass-line of the web between the source and detector. The pass-line is used with a correcting function to correct the nuclear readings and provide a substantially accurate measure of web thickness corrected for pass-line. The very direct paths for both types of radiation and the rugged nature of the assembly assures reliable operation in industrial environments.

24 Claims, 3 Drawing Sheets

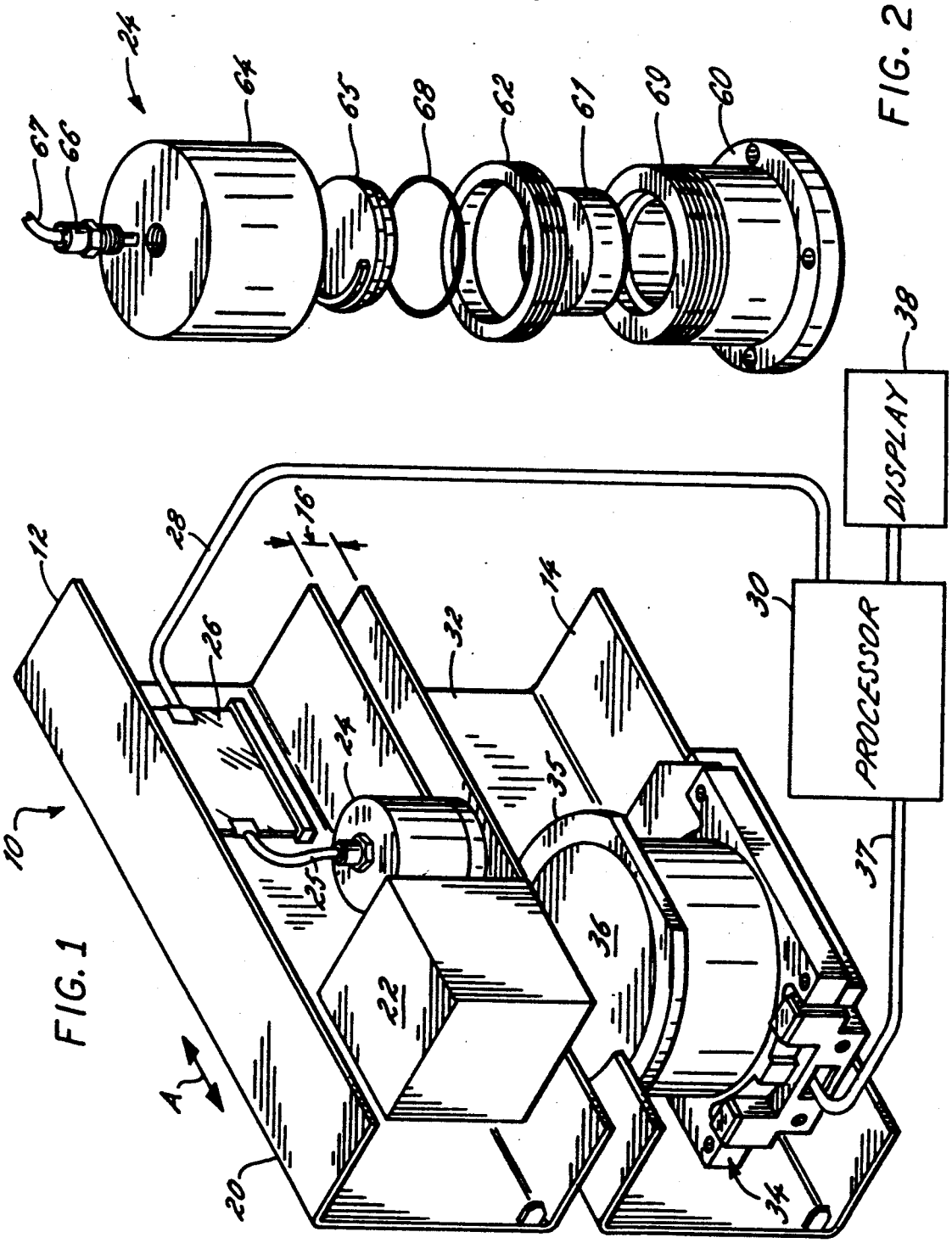

PASS-LINE INDEPENDENT WEB MEASURING METHOD AND APPARATUS

FIELD OF THE INVENTION

This invention relates to web thickness measuring, and more particularly to measuring thickness related parameters such as thickness, density, basis weight, or the like of a moving web.

BACKGROUND OF THE INVENTION

In forming sheets of material, such as plastics, paper or other materials, the materials generally are formed in a continuous process as a moving film or web. In order to most effectively monitor and control the process, one or more properties of the web must be determined while the web is in motion. The properties which are of interest here are termed "thickness related properties" and include in particular circumstances web thickness, caliper, density, basis weight, or others. Further, in many cases it is important to measure web profile variations, such as streaks and hence the web property needs to be measured across the width of the moving web.

To measure the desired web property, one or more sheet sensors are employed in fixed or web traversing structures. The moving web can be constrained to move over a fixed reference surface, but more commonly the moving web is unsupported in the measurement region and is subject to deviations from the nominal path through the measurement region. The nominal path through the measurement region is usually referred to as a "pass-line", and deviations from that pass-line such as "flutter" or other lower frequency deviations alter the pass-line of the web through the measurement region.

A desirable method of forming a measurement region across the width of the web, is to utilize nuclear radiation in a traveling sensor arrangement which traverses the moving web to measure the desired web property. A radioactive thickness/density gauge is based upon the principle that a mass of material will absorb the products of radioactive emission in a known and repeatable manner. An industrial web gauging instrument, known as a beta-gauge, typically utilizes a radioactive isotope which decays through beta particle emission. The radioactive isotope is mounted in an enclosed head or source, which projects the radiation through the web to a second head or detector which includes a radiation detector. The amount of radiation sensed by the detector is directly related to the amount of radiation absorbed by the web material being measured.

The absorption of beta particles by matter or material is shown by the following equation:

$$N = N_o(1 - e^{-\alpha d})$$

where N is equal to the amount of beta radiation absorbed by the material, $N_o$ is the amount of beta radiation incident on the material prior to absorption, $\alpha$ is a constant related the type of material (which primarily is a function of the material density) and d is the thickness of the material. The signal generated by the detector thus can be utilized in an instrument to accurately and repeatedly solve for the material thickness.

The relative position of the moving web in the measurement region space between the source and detector heads is called the web pass-line. Due to the nature of beta particle interaction with the web material, specifically due to the angular dispersion of the beta particles as they pass through the web, the amount of radiation sensed by the detector varies with pass-line deviations. Since the fluctuating web pass-line can vary significantly and at a high frequency during a measurement of the moving web, the accuracy of the gauge or sensor in part depends on the ability to compensate for pass-line variations.

The prior art has compensated for pass-line variations in a variety of manners. One prior art compensating method is to employ a radiation absorption shading strip or disc on the detector to geometrically flatten the radiation intensity profile entering the detector. The shading strip in effect smooths the radiation profile, thus making the source-detector geometry less sensitive to pass-line variations. However, it is clear that this approach, while it reduces the sensitivity to pass-line variation, also reduces the sensitivity of the system. The result is reduction in the ability of the measuring system to resolve small changes in moving web thickness, or the ability to identify the presence of small streaks on the moving web. Further, the shading strip or disc also requires precise alignment between the source and detector in both the initial setup of the gauge and during transverse scanning of the moving web. The alignment tolerance can be on the order of ±0.005 inches, which tolerance is virtually impossible to maintain across the moving web width, which typically is a width of sixty (60) inches. This results in significant inaccuracy in the thickness measurements of the moving web.

Another approach to minimizing the effect of pass-line variations is to simply reduce the speed of response of the sensor, thereby obtaining a slowly responding average of the target thickness. While that approach also reduces the effect of pass-line variation, it is clear that it does so at the expense of streak resolution and the ability to respond to small thickness variations in the web.

Another prior art, for example, is Watson U.S. Pat. No. 4,276,480, which discloses various embodiments of optical sensors for measuring web thickness, and utilizes one such device in combination with a nuclear detector to produce a correction function relating nuclear sensor response to variations in pass-line position. The approach suggested in the '480 patent is deficient for a number of reasons, a primary reason being the rather complicated optical system utilized in illuminating the web with a spot of intense radiation, then sensing the change in spot position resulting from deviation in web position. The optical system includes a rather complex optical path in order to allow for the generation of light, its deflection onto the web, its deflection from the web and its collection on a linear detector all in a single housing. The optical system also suffers from additional defects in an industrial environment of being susceptible to erratic operation if not maintained adequately clean, as well as erratic operation that can result when producing a web of non-uniform reflectivity. In short, it does not appear that the proposed device is adequate in all respects to meet the demands of the industrial environment.

It would be desirable to reliably eliminate pass-line variations from the moving web measurements in the industrial environment, while still providing sensitivity to small variations in the moving web thickness and sensitivity to streaks on the moving web.

SUMMARY OF THE INVENTION

In view of the foregoing, it is a general aim of the present invention to reliably eliminate inaccuracies in moving web measurements due to pass-line variations, while maintaining sensitivity to streaks and small thickness variations.

In a more detailed aspect, it is an object of the present invention to provide a web thickness measuring system which include compensation for pass-line variations implemented in a non-complex and reliable manner, commensurate with the reliability of the thickness measuring elements themselves.

Broadly in accomplishing those objects, the invention provides a source of nuclear radiation and a nuclear detector mounted in a housing in a fixed relationship with respect to each other to direct radiation toward the web and detect radiation from the web. Processor means responds to a measure of the radiation received by the detector from the web for producing an uncorrected measure relating to web thickness. The measure is uncorrected with respect to the actual web pass-line. Distance measuring means is mounted in the housing and has an output transducer aimed directly at the web for directing energy at the web and an input transducer aimed directly at the web for receiving at least a portion of the directed energy from the web. Means responsive to the received energy determines the actual web pass-line. Compensating means then compensates the uncorrected measure relating to web thickness in accordance with the actual web pass-line as measured to produce a measure of thickness corrected for actual pass-line.

Preferably, the distance measuring means is an ultrasonic source, but other sources such as magnetic, optical or electrical can accomplish certain of the objects of the present invention. Nuclear radiation source is preferably a beta measuring system with a source mounted on one side of the web and a sensor on the other. However, certain of the objects of the invention can be achieved by a source/detector combination mounted in a single housing on the same side of the web, such as a gamma detector relying on back scatter.

In its preferred aspects, the invention provides a measuring system based on a nuclear source and sensor which project radiation directly through the web for making uncorrected thickness related measurements of a moving web. Thickness related measurements as used herein are intended to encompass not only thickness or caliper per se, but also other thickness-type measurements such as basis weight or density. An ultrasonic distance measuring means is fixedly mounted with respect to either the nuclear source or detector, and is aimed at the web for transmitting pulses of ultrasonic energy on a path which is substantially normal to the web, and detecting pulses reflected from the web on substantially the same path. The time delay between a transmitted and reflected pulse is a measure of the actual web pass-line at the time of the pulse. That information is utilized along with a correcting function which relates pass-line variations to corrections to be applied to the uncorrected thickness measurement. Thus, corrections for pass-line variation are reliably made even in an industrial environment susceptible to contamination.

It is a feature of the preferred embodiment of the invention that the paths for travel of radiation between the nuclear source and detector which measure web thickness and the ultrasonic source and sensor which measure pass-line variation are similar and direct. The former is in a straight line from the source to the opposed detector through the web. The latter is in a similar straight line but rather than passing through the web, it is reflected back to its origin. Thus, although the paths are similar, one is folded and relies on both the source and sensor being in the same housing to sense pass-line variation.

Other objects and advantages will become apparent from the following detailed description when taken in conjunction with the drawings in which:

BRIEF DESCRIPTION OF THE DRAWINGS

FIG. 1 is a perspective view of one embodiment of web thickness measuring system exemplifying the present invention;

FIG. 2 is an exploded perspective view showing further details of the ultrasonic distance measuring portion of the system of FIG. 1;

DETAILED DESCRIPTION OF THE PREFERRED EMBODIMENTS

Figure 3:
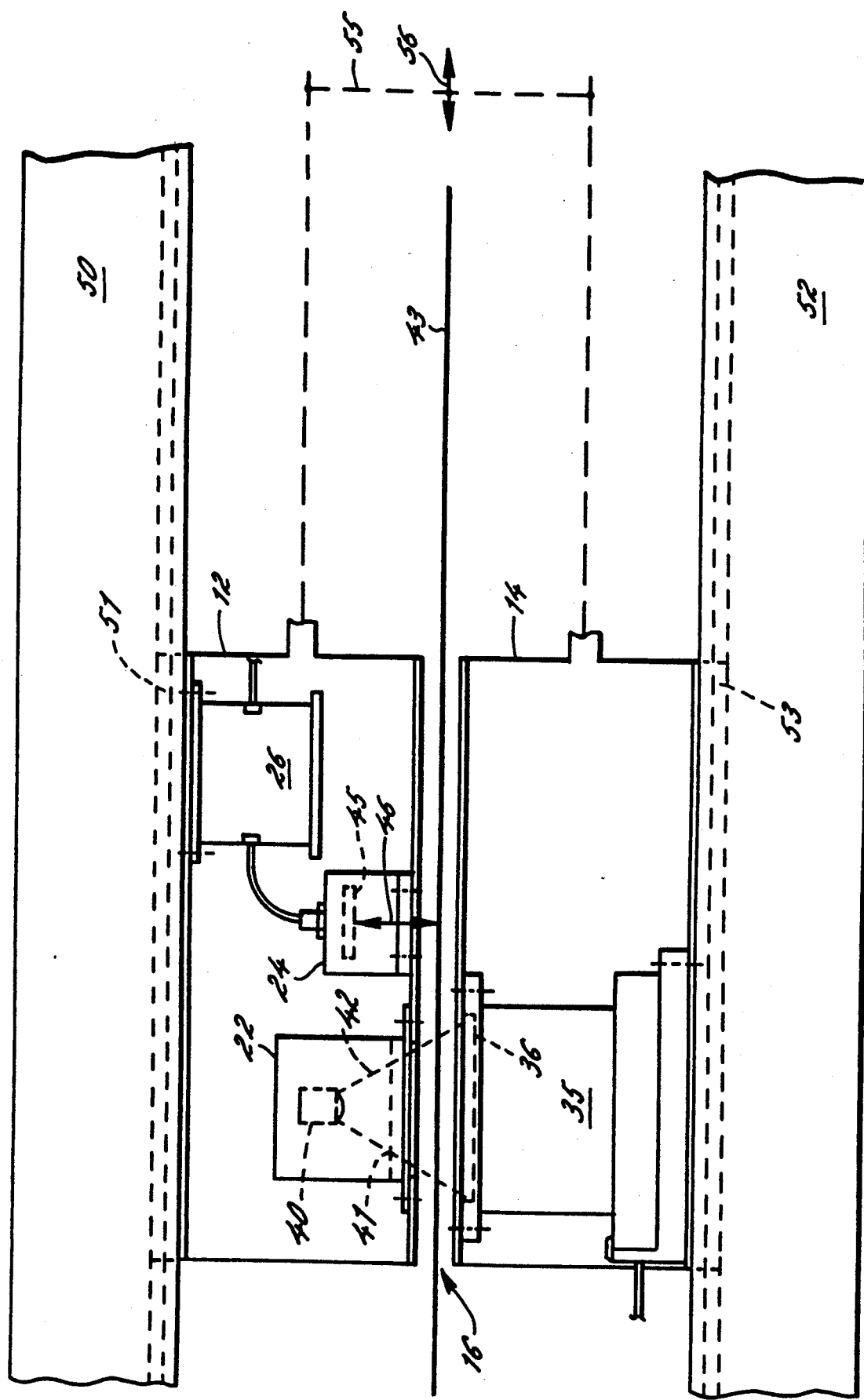
FIG. 3 is a diagram illustrating source and detector associated with a web to be sensed, further illustrating a system exemplifying the present invention.

While the invention will be described in connection with a preferred embodiment, there is no intent to limit it to that embodiment. On the contrary, the intent is to cover all alternatives, modifications and equivalents included within the spirit and scope of the invention as defined by the appended claims.

Turning now to the drawings, FIG. 1 illustrates the major elements of a pass-line independent web measuring device for producing thickness related measurements of a moving web, such device being generally indicated by the reference character 10. It is seen that the device 10 is comprised of two major elements, a source head 12 and a sensor head 14. The heads 12, 14 are mounted in fixed relation with respect to each other to produce a gap 16 therebetween. The gap 16 accommodates the travel of the web 43 to be measured (see FIG. 3). As will also be described in greater detail below, the source and detector heads 12, 14 are usually mounted for traverse across the moving web, the traverse direction being denoted by the arrow A shown in FIG. 1, with the direction of web travel being normal to the direction of arrow A through the gap 16. It is conventional to establish a predetermined line normally centered in the gap 16 as the expected pass-line for web travel, and as pointed out above, in the prior art when the web deviated from such pass-line, thickness measurements produced by the device did not meet the desired accuracy requirements.

Referring in greater detail to the elements which make up the measuring system 10, it is seen that the source assembly 12 is based on a housing member 20 on which is mounted a nuclear source 22. The source 22 is fixedly mounted on the bracket 20 and has an aperture of predetermined shape and dimension aimed at the gap 16 and thus at the web in the gap, as better illustrated in FIG. 3. Because the source 22 is typically smaller than the detector in the opposite housing, it is convenient to mount the pass-line sensor in the source housing 20. The position of the pass-line sensor in the source housing also serves to mount such sensor with its aperture downward so as to prevent collection of debris or the like in the open sensor window. Housing 20 thus makes provision for mounting of ultrasonic sensor 24 which, like the source 22 is fixed to the housing 20 and thus is in a predetermined relationship with gap 16 and the detector housing 14. Ultrasonic sensor 24, as will be described in greater detail below, emits pulses of ultrasonic radiation at the web in the gap 16 on a path substantially normal to the web, and detects reflections from the web on substantially the same normal path. Circuitry mounted in circuit board 26 is coupled to the sensor 24 by means of a cable 25 and thus controls the transmission of pulses, senses the receipt of reflections, and determines by means of the delay between a pulse and its reflection the actual position of the web in the gap 16. It will be appreciated that while the system is capable of determining the actual pass-line position, the system can also be arranged, if desired, to measure deviations from a desired pass-line position. Suffice it to say, that the ultrasonic sensor 24 operating in conjunction with circuitry 26 determines the position of the actual pass-line in the gap 16 and thus is capable of producing a compensating signal for the thickness measuring circuitry. Such compensating signal is coupled on a cable 28 to processor 30 which will be described in greater detail below.

Turning then to the detector assembly 14, it is seen that such detector is also formed on a rigid housing member 32 which provides a secure mounting surface for detector means 34. The detector 34 preferably includes an ionization chamber 35 having a window 36 for receiving beta radiation emanating from the source 22 which penetrates the web in the gap 16. Thus, the ionization chamber 35 is adapted to provide an electrical signal responsive to the amount of radiation which penetrates window 36 in the ionization chamber 35. Such electrical signal is coupled by means of cable 37 to the processor 30. The signal can be in the form of counts which represent pulses of radiation received, or in the form of an analog signal which is proportional to the amount of radiation received. In any event, the signal coupled to the processor 30 on line 37 is a measure of the radiation emanating from the source 22 which has penetrated the web in the gap 16. Since the intensity of the source 22 is known, processor 30 has the information necessary to determine, based on the amount of radiation received by the detector 34, the amount of radiation which had been absorbed in the web. The processor then utilizes known techniques and circuits for producing an indication of the web thickness parameter desired, and displays that parameter on a display 38. The display 38 can be in the form of a visual readout, a paper printout, or can be a magnetic recording for later computerized processing and display. In any event, the processor 30 keeps a running record of web thickness both along the web as the web is produced, and across the web as the detector traverses the web, and displays that information in a desired format.

FIG. 1 illustrates the source and detector assemblies 12, 14 as open structures primarily for convenience in showing the internal components. In an industrial environment, both assemblies will typically be enclosed, and as will be further described in connection with FIG. 3, mounted on a frame such as a O-frame for traverse in unison across the web in a fixed relation with respect to each other.

The nuclear source and detector are not shown in greater detail in the drawings since they can be conventional. More particularly, it is preferred to use the elements commercially provided under the trademark BETAMIKE of the Barber-Colman Company. As better illustrated in FIG. 3, the source assembly 22 includes a radioisotope source (which can be considered a point source) 40 which is collimated at 41 to produce a beam 42 of predetermined shape and intensity of beta particles emitted from the source 40. FIG. 3 demonstrates that the shaped beam 42 passes through the web 43 positioned in the gap 16 and is directed to the window 36 of ionization chamber 35. It will be appreciated that no shields are needed at the window 36 in order to restrict the geometrical span of the beam 42 in view of the pass-line compensation taught herein.

FIG. 3 also illustrates the pass-line position sensor comprising ultrasonic sensing device 24 mounted in the housing 12 on the same base plate as the source 22. It will be appreciated that if room permitted, the source could as well be mounted in housing 14. It is seen that the ultrasonic sensor includes a transducer schematically illustrated at 45 which is used both as a source of ultrasonic pulses and as an ultrasonic receiver. In an alternative embodiment, different transducers can be utilized if desirable, but in any event, the transducers will either be the same or very closely spaced. There is at least one exception to that general desirability, and that is the case where relatively high frequency web fluctuations can be expected. In that case, in order to assure that both the nuclear sensor and the pass-line sensor are sensing the same portion of the web, a further pass-line sensor 24' is located on the left-hand side of source 22 (see FIG. 1) in a mirror position to pass-line sensor 24. The sensor 24 emits radiation at a slight angle at the web positioned intermediate the source 22 and detector 36, the energy being emitted by the transducer in pass-line sensor 24 being reflected from the web to the second pass-line sensor 24'. Thus, the web portion intermediate the nuclear source and detector 22, 36 is also the portion which reflects the ultrasonic energy for pass-line determination. It will be appreciated that in this altered embodiment the pass-line energy transmission and reflection are very similar, are both very direct, and are of substantially the same length. In cases where high frequency fluctuation is not expected to be a significant problem, however, because of its simplicity and even more directly substantially normal paths, only a single transducer 24 which functions as both the source and receiver of ultrasonic radiation is preferred.

In the various embodiment, the ultrasonic path illustrated by double-headed arrow 46 represents both the beam of energy transmitted at the web 43 substantially normal to its surface and the reflected beam returned directly to the transducer 45. It will be appreciated that flutter in the web which might slightly misalign the web locally with respect to the transducer is of no moment since the beam of energy transmitted to the web and the broader beam reflected to the sensor will ultimately cause the position of the sheet 43 to be detected even during the course of local misalignment. FIG. 3 also demonstrates the direct path of ultrasonic radiation and that similarity of the path to that of the nuclear sensor. Thus, where the nuclear source 22 is positioned opposite its detector 34 and transmits its energy directly through the web, the transmission path with respect to ultrasonic sensor 24 can be considered a folded version of the nuclear transmission path. Thus, both travel paths are of about the same short length and the same straightforward simplicity underlying the reliability of the device. Furthermore, as will be better appreciated in connection with FIG. 2, like the industrially packaged BETAMIKE nuclear elements, the ultrasonic sensor 24 is also packaged to withstand the industrial environment. No lenses or the like are need, the ultrasonic energy is emitted near the base of the housing 12 directly at the web 43 and is similarly received in the same location at the base of housing 12, and does not require lenses or the like for focusing or deflection in order to perform its intended function.

Before referring in greater detail to the construction of the ultrasonic sensor 24, attention will first be directed to the mounting for the source head 12 and detector head 14 as schematically illustrated in FIG. 3. FIG. 3 shows guide means comprising a pair of guides 50, 52 which engage tracks 51, 53 schematically illustrated on the source and detector heads 12, 14. The dotted line 55 suggests that the source and detector heads 12, 14 are mounted in the guide means for traverse (in the direction indicated by arrow 56) in unison and thus are, in effect, fixed with respect to each other. As is known, the relative position of the source and detector is fixed by means of the mechanical and electrical components of the traversing drive, and the link 55 is intended to schematically represent that function and not a direct mechanical link which would interfere with web travel between source and detector. With the source and detector fixed in position with respect to each other during a scanning traverse, the only variable in web detection is the pass-line position, i.e., the position of web 43 in the gap 16, which has been discussed in detail herein. In cases of very wide webs requiring a substantial traverse, there may be sufficient sag in the mechanical system as to make it desirable to check that gap between the source housing and sensor housing has not changed. In that case, it may be desirable to include a second pass-line sensor 24" mounted in the receiver housing in a position similar to that of pass-line sensor 24, such that the position of the web with respect to both housings is determined for an even further refined pass-line corrected thickness measurement. However, it will be appreciated that in most cases the mechanics of the traversing system are sufficiently rigid and the web widths sufficiently narrow that only a single transducer as is preferred is required.

Turning then to FIG. 2, the currently preferred embodiment for the ultrasonic sensor 24 is illustrated in exploded form. The housing has a base plate 60 which is apertured for secure mounting to the housing 12 of the transmitter head, bearing a substantially unobstructed path for coupling of ultrasonic energy into the gap 16. A filter 61 is provided to maintain the cleanliness of the inside of the housing and provide a material of known acoustic characteristic through which the ultrasound waves will pass. A mounting ring 62 has a threaded exterior adapted to mate with internal threads in a housing cover 64. Mounted within the housing cover 64 is a commercially available ultrasonic transducer 65 which contains the ultrasonic source and detector diagrammatically illustrated at 45 in FIG. 3. A connector 66 which couples a cable 67 to the housing 64 is connected to the ultrasonic transducer 65 for coupling energy to the transducer for transmission toward the web, and for coupling signals resulting from receipt of energy in the transducer toward the sensing circuitry. When the unit is assembled, the ultrasonic transducer 65 is inserted within the cover 64, an O-ring 68 put in place for sealing the assembly, then the mounting ring 62 threaded into the cover 64 to secure the transducer 65 in place. Filter 61 having been located in the body 60, the cover 64 is then positioned over the threaded exterior 69 of the housing 60 and secured in place. The unit is then mounted in place on the housing member 20 and cable 67 connected to circuit board 26 which contains the electrical circuitry for generating the ultrasonic pulses, detecting the ultrasonic reflections, and calculating the delay between them as a measure of distance of the reflector, in this case the web, from the transducer.

Figure 4:
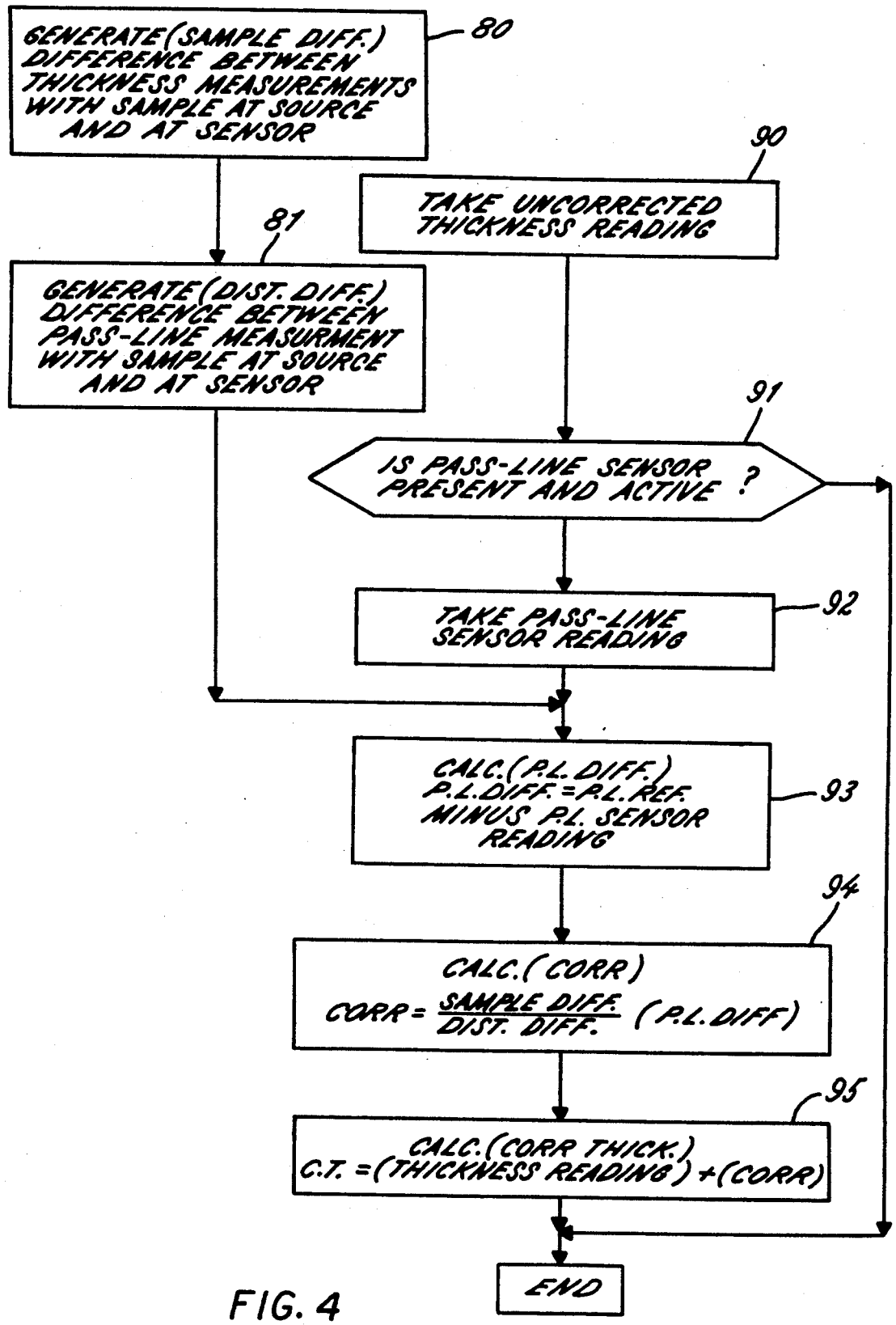
FIG. 4 is a flowchart showing process steps for determining pass-line corrections and applying those corrections in measuring web thickness according to the present invention.

Attention will now be directed to FIG. 4 which shows the manner in which the processor 30 of FIG. 1 combines the signals from the nuclear source and detector 22, 34 and the ultrasonic sensor 24 to produce corrected readings related to the thickness of the web passed between those elements. A first pair of steps 80, 81 are used in calibration of the system, and should be repeated periodically but are not normally performed when the device is operating to measure thickness of a running web. However, the calibration steps should be repeated whenever the caliper or type of material being produced is changed, since the correction factors vary with material thickness and with material type. It will be appreciated that the correcting function can only be generated for a nominal thickness, and it is appreciated that for reasonable variations from that nominal thickness the correcting function will apply. However, when a material of a substantially different thickness is to be produced, a new correcting function which potentially has a different slope should be obtained.

Assuming it is desired to set up the system for running with a web of a particular type and caliper, a sample of that material is obtained, and in a first step 80 an operation is performed to determine the thickness sample differential for two positions of the web in the gap 16. Concurrently, a second step 81 is performed to determine the pass-line sensor differential, i.e., a differential measured by the pass-line sensor 24 for the sample in the same two extreme positions. Thus, with the sample is place in the gap 16 at a position near the source 22, i.e., in contact with the lower portion of the housing 12, the steps 80 and 81 are performed. With the sample so held, the step 80 determines the sample reading produced by the nuclear source and detector for that position and the step 81 determines the pass-line sensor distance reading produced by the pass-line sensor 24. Those measurements preferably in the form of analog-to-digital converter (A/D) counts are then stored. The sample is then moved to a second extreme position near the detector 34, such as in contact with the lower housing 14. The same steps 80, 81 are performed to determine a sample reading for the nuclear system and a pass-line reading for the distance system, and those samples are also stored. The extreme sample readings and the extreme distance readings are then combined to determine the difference therebetween, and represent the sample and pass-line differentials to be used in later processing. More particularly, what has been determined is the extreme sample reading if the web were in contact with the source 22 and the extreme reading with the web in contact with the detector 34, and the difference between those two readings to determine the variation which can be attributable to pass-line position deviating in the gap 16. Similarly, readings are taken from the pass-line sensor 24 to determine the output of that system with the web in contact with the sensor 24 on one extreme and distant from the sensor 24 on the other extreme, and those readings are subtracted to determine the maximum differential reading or full scale pass-line variation in the gap.

The calibration steps yield the total change in sample reading and the total change in pass-line reading for the two extreme conditions and thus can be divided, one by the other, to yield the slope of a correcting function relating sample difference to changes in pass-line difference in the gap. The opportunity to produce such a correcting function and to apply such function is significant in achieving the objects of the invention. In the particular implementation of the invention here being discussed, the application of the correction is by way of the slope of the correcting function, and that is important only in the particular implementation rather than the invention broadly. However, in that particular implementation, it is further noted that the most accurate reading obtainable from the nuclear system for a thickness measurement is that achieved with the sample in contact with the detector. In the preferred form of the invention, the processing circuitry takes advantage of that characteristic and corrects all readings to those which would have been obtained had the web been at the detector rather than its actual pass line.

Thus, with the calibration steps accomplished, and the correcting function for the particular sample derived, the running of the program can start at a step 90 in which an uncorrected thickness measurement is made by sampling the nuclear detector. A step 91 is then performed to determine if the system has a pass-line sensor and if said sensor is active. If it is not, the program terminates. If it is, the system then proceeds to a step 92 which takes a pass-line sensor reading to determine the position of the web within the gap 16. This reading is taken at approximately the same time as the actual nuclear reading in the step 90. Having thus determined an uncorrected thickness reading in step 90 and an indication of actual pass-line position in the step 92, steps 93 and 94 are performed to determine the correction which should be applied to the uncorrected reading taken at step 90 position. In the example of the present invention, the correction will add a sample signal to the actual sample measurement to create a corrected sample reading which would be taken by the system had the web been immediately adjacent the detector.

Accordingly, the step 93 determines the actual pass-line position with respect to the given reference (at the detector). Step 93 is similar to step 81 in that it subtracts A/D counts generated by the pass-line sensor 24 for two different positions. In the step 93, the positions are first a reference position with the sample on the detector (as determined at step 81) and the second position is the actual pass-line determined in step 92. The pass-line difference thus generated in step 93 creates a measure of actual pass-line in the gap 16. Step 94 is then performed to determine a correction to be applied to the uncorrected reading 90.

Step 94 first determines the slope of the correcting function by dividing sample difference (determined in calibration step 80) by the distance difference (determined in calibration step 81). The slope of that correcting function is then multiplied by the result of step 93, i.e., by the pass-line difference signal) to determine the number of sample counts (in an A/D system) by which a sample of a given thickness at the pass-line would differ from a sample of the same thickness if located at the detector. That value is the result of the computation in step 94. In order to then compute the corrected measure of web thickness, the value determined in step 94 is added to the actual sample measurement taken in step 90 to produce a resultant sample signal. The resultant total is the sample value for the nuclear system translated by an amount determined by actual web position as determined by the pass-line sensor.

The improvement is two-fold. First of all, pass-line deviations are accurately accounted for. Secondly, in the preferred embodiment, where the nuclear system produces its most accurate reading with the web in a position where it cannot physically be sensed, i.e., in contact with the detector, the system can make the necessary computation to produce a reading equivalent to that desirable but impractical measurement. Calibration is thus easier. The system or operator need not rely on samples positioned at an intermediate pass-line position in the calibration procedure. The samples can be positioned right on the source and right on the detector to determine calibration readings at those positions. Having thus obtained those calibration readings, all actual measurements generated during the course of the run can be translated to the most accurate position in the system, in the example to the reading with the web in contact with the detector, and that correction accommodates for pass-line deviations and does so in such a way as to translate all readings to the most accurate reference in the system.

It is emphasized that the flowchart of FIG. 4 is merely exemplary of one manner of processing the signals which are produced by the system. The basis for the processing is the fact that the system is calibrated to produce pass-line difference signals which can be compared with the actual pass-line signal generated by the same transducer. The system also during calibration produces difference signals relating to the nuclear scanner which are generated at the two extremes, and that information allows the system, based on the actual pass-line position measured by the pass-line sensor 24, to determine a correction based on actual pass-line position, and apply that correction to the signal then measured by the nuclear source and detector.

In the most preferred form of the invention, the time constant of both the nuclear system and the ultrasonic system are set to be about the same, and to correlate with maximum speed and the maximum expected rate of change of the parameter being measured in the web. In one example, the sampling rate is set at about 10 milliseconds. That allows approximately 10 milliseconds for integration of a count in the nuclear system and that provides good resolution commensurate with reasonable speed of travel of the web. When a 10 millisecond integrating period is used in the nuclear detector, the ultrasonic system is also set to utilize about a 10 millisecond sampling interval to produce a new measurement of pass-line position about every 10 milliseconds. When those measurements are taken approximately concurrently, information is available to the processor relating to the thickness and the pass-line position of the same portion of web as sensed by both systems.

The specification herein has emphasized the preferred embodiment of the invention which utilizes a beta source and beta sensor in separate housings on opposite sides of the web and a single ultrasonic detector mounted in one of the housings for determining the actual web pass-line. Certain of the advantages of the invention can be achieved in lesser preferred embodiments. For example, gamma gauges utilizing back-scatter principles mount both a nuclear source and detector in a housing on the same side of the web to measure thickness-related properties. Certain of the advantages can be achieved by also associating a pass-line sensor in accordance with the invention in that system.

While ultrasonic pass-line sensors are preferred for their ruggedness, simplicity and comparative economy, pass-line sensors using other principles can achieve certain of the advantages of the invention. For example, optical systems using very direct and non-folded paths and in some cases adequately measure pass-line deviations. Other electrical or magnetic systems can also be applied such as those for measuring magnetic fluctuations in connection with conductive sheets, those for sensing capacitive changes and the like.

It will now be appreciated that what has been provided is a practical, efficient and accurate system for providing thickness or caliper measurements of a moving web. In the preferred embodiment, a well-proven nuclear source and detector system is utilized to provide thickness measurements, but one which can suffer from inaccuracies due to pass-line deviation. An ultrasonic sensor is mounted in the housing with one of the nuclear elements so as to maintain a predetermined spatial relation with the nuclear system. The pass-line sensor operates on ultrasonic principals which reliably function in an industrial environment without the necessity for taking any greater care of the sensing elements than had been taken of the commercially available nuclear equipment in the past. Significantly, the ultrasonic system can be added to the conventional nuclear system at a very minor incremental cost to achieve a substantial improvement in the accuracy and reliability of sensed web thicknesses. The ultrasonic system utilizes a direct sensing path for determining pass-line position, and relating actual pass-line position to a known datum referenced to the nuclear system. The energy which is utilized to make the pass-line measurements traverses a path very similar to that traversed by the nuclear energy which generates the thickness measurements. The measurements are combined in a processor already provided for the thickness measurements, and thus, operating with substantially the same equipment as has been used in the past, operators are now able to more accurately produce thickness measurements irrespective of the actual pass-line of the web through the equipment.

What is claimed is:

1. A pass-line independent web measuring device for producing thickness related measurements of a moving web, the measuring device including housing means mounted adjacent the web and establishing a pass-line for the web with respect to the housing means, the measuring device comprising, in combination:
   a source of nuclear radiation and a nuclear detector mounted in the housing means in a fixed relationship with respect to each other to direct radiation toward the web and detect radiation from the web;
   processor means responsive to a measure of the radiation received by the detector for producing an uncorrected measure relating to web thickness, said measure relating to web thickness being uncorrected with respect to the actual pass-line of the web;
   distance measuring means mounted in said housing means, the distance measuring means having output transducer means aimed directly at the web for directing energy at the web and input transducer means aimed directly at the web for receiving at least a portion of the directed energy from the web, and means responsive to the received energy for determining a measure of the distance traveled by said energy between the output transducer, the web and the input transducer to determine the actual web pass-line, the actual web-pass-line relating to the distance between the housing means and the web measured substantially normal to the web; and
   means for compensating the uncorrected measure relating to web thickness in accordance with the actual web pass-line determined by the distance measuring means to produce a measure corrected for pass-line relating to web thickness.

2. The combination as set forth in claim 1 further including integrating means associated with the processor means for establishing a time interval for detecting radiation received from the source detected by the detector, the distance measuring means including means for directing energy at the web and receiving energy from the web for a measuring period compatible with said integrating interval.

3. The combination as set forth in claim 1 wherein the housing means includes a source housing and a detector housing mounted on opposite sides of the web having a pass-line therebetween.

4. The combination as set forth in claim 1 wherein the compensating means further includes means for storing a relationship between pass-line and thickness corrections for providing correcting values in dependence upon actual web pass-line.

5. The combination as set forth in claim 1 wherein the housing means further includes means for mounting the housing for traverse across the width of the web to reproduce thickness related measurements across the web width.

6. A pass-line independent web measuring device for producing thickness related measurements of a moving web, the measuring device including housing means mounted adjacent the web and establishing a pass-line for the web with respect to the housing means, the measuring device comprising, in combination:
   a source of nuclear radiation and a nuclear detector mounted in the housing means in a fixed relationship with respect to the each other to direct radiation toward the web and detect radiation from the web;
   processor means responsive to a measure of the radiation received by the detector for producing an uncorrected measure relating to web thickness, said measure relating to web thickness being uncorrected with respect to the actual pass-line of the web;
   ultrasonic distance measuring means mounted in said housing means for directing pulses of ultrasonic energy at the web and receiving reflected pulses from the web along direct paths of substantially the same length, the time delay between a pulse and its reflection being a measure of the actual web pass-line; and
   means for compensating the uncorrected measure relating to web thickness in accordance with the actual web pass-line determined by the ultrasonic means to produce a measure corrected for pass-line relating to web thickness.

7. The combination as set forth in claim 6 wherein the housing means comprise first and second housings mounted on opposite sides of the web for establishing a pass-line therebetween, the source of nuclear radiation being mounted in one of said housings and the nuclear detector in the other, the ultrasonic distance measuring means being mounted in at least one of said housings.

8. The combination as set forth in claim 7 wherein the ultrasonic distance measuring means includes a transducer aimed at the web for directing pulses of ultrasonic energy at the web and receiving reflected pulses from the web along subtantially the same path.

9. The combination as set forth in claim 7 further including guide means for mounting the first and second housings on opposite sides of the web for traverse across the web in a direction substantially normal to web movement, the guide means serving to maintain said fixed relationship between the nuclear source and nuclear detector during traverse of the housings across the web.

10. The combination as set forth in claim 9 wherein the ultrasonic distance measuring means includes a transducer aimed directly at the web for directing ultrasonic pulses at the web in a path substantially normal thereto and receiving ultrasonic reflections from the web in substantially the same normal path, the ultrasonic distance measuring means being fixedly mounted in one of said housings to maintain the substantially normal path for ultrasonic pulses during traverse of the housing across the web.

11. The combination as set forth in claim 10 wherein the ultrasonic distance measuring means includes a single transducer which generates said pulses and detects said reflected pulses along said substantially normal path.

12. The combination as set forth in claim 7 further including integrating means associated with the processor means for establishing a time interval for detecting nuclear radiation received from the web, the ultrasonic means including means for directing said pulses of ultrasonic energy and receiving reflected pulses for a measuring period compatible with said integrating interval.

13. The combination as set forth in claim 7 wherein the nuclear radiation source is a source of beta radiation aimed to impinge on the web, and the nuclear detector is a beta detector aimed at the web for recovering beta radiation emitted by the source passed through the web to the detector.

14. The combination as set forth in claim 13 wherein the integrating interval of the processor means and the measuring period of the ultrasonic means run substantially concurrently so as to compensate for time varying fluctuations in pass-line.

15. The combination as set forth in claim 14 wherein the measuring period of the ultrasonic means is sufficiently short to detect fluctuations in said pass-line but sufficiently long to maintain compatibility with the integrating interval of the processor means.

16. The combination as set forth in claim 13 further including an analog-to-digital converter connected to count pulses produced by the nuclear detector in response to receipt of beta radiation from the nuclear source which is not absorbed in the web, the compensating means including means for generating a correcting count based on the actual web pass-line, and means combining the correcting count with the detected count to produce the corrected measure relating to web thickness.

17. The combination as set forth in claim 16 wherein the compensating means further includes means for storing a relationship between pass-line and thickness corrections for providing correcting values in dependence upon actual web pass-line.

18. The combination as set forth in claim 17 wherein the relationship between pass-line and thickness corrections comprises a function relating pass-line and thickness measurements with a sample positioned at the source of nuclear radiation in one condition and at the nuclear detector in the other condition.

19. The combination as set forth in claim 18 wherein said correcting values translate the uncorrected measure relating to web thickness taken at the actual pass-line to a corrected measure of web thickness at the nuclear detector.

20. The combination as set forth in claim 6 wherein the compensating means further includes means for storing a relationship between pass-line positions and thickness corrections for providing correcting values in dependence upon actual web pass-line.

21. A method of producing thickness related measurements of a moving web having a pass-line associated with a source and detector aimed at the web and fixed with respect to each other, wherein the web pass-line can deviate from a desired pass-line position with respect to the source and detector, the method comprising the steps of:

directing nuclear radiation from the source to the detector by way of the web and detecting radiation emitted by the source and directed to the detector by the web which is therefore an uncorrected measure related to the thickness of the web;

concurrently with the directing and detecting of nuclear energy step, directing non-nuclear energy at the web in a first direct path and detecting reflected energy from the web along a second direct path of substantially the same length as the first direct path, determining the actual pass-line of the web based on the energy reflected from the web;

establishing and storing a correcting function relating pass-line position to a thickness correcting function; and altering the measure related to uncorrected thickness by a value determined from the particular correcting function related to the actual determined pass-line.

22. A method of producing thickness related measurements of a moving web having a pass-line between a source and detector aimed at and fixed with respect to each other, but wherein the web pass-line can deviate from a desired pass-line position between the source and detector, the method comprising the steps of:

directing nuclear radiation from the source to the detector through the web and detecting the radiation emitted by the source and passed through the web and is therefore an uncorrected measure related to the thickness of the web;

concurrently with the directing and detecting step, aiming ultrasonic pulses at the web in a direction substantially normal to the web, detecting ultrasound reflections from the web along substantially the same path, and measuring the delay between directed and reflected pulses as a measure of the actual web pass-line;

establishing and storing a correcting function relating pass-line position to a thickness correcting function; and altering the measure related to uncorrected thickness by a value determined from the particular correcting function related to the actual pass-line determined by said ultrasonic directing and detecting.

23. The method as set forth in claim 22 wherein the step of establishing a correcting function further comprises measuring the detector output to produce a first correcting reading when the web is in a predetermined relationship near the detector, measuring the detector output to produce a second correcting reading when the web is in a predetermined relationship near the radiation source, and producing the correcting function as a continuous function joining the first and second correcting readings.

24. The method as set forth in claim 23 wherein the step of altering further comprises altering the measure related to uncorrected thickness by a valve which would translate the actual pass-line to the pass-line at the detector.

* * * * *